(12) United States Patent
May

(10) Patent No.: US 11,672,953 B2
(45) Date of Patent: Jun. 13, 2023

(54) TORQUE DEVICES FOR USE WITH INTRAVASCULAR DEVICES AND ASSOCIATED SYSTEMS AND METHODS

(71) Applicant: KONINKLIJKE PHILIPS N.V., Eindhoven (NL)

(72) Inventor: Justin May, Ladera Ranch, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 276 days.

(21) Appl. No.: 16/836,222

(22) Filed: Mar. 31, 2020

(65) Prior Publication Data

US 2020/0222663 A1 Jul. 16, 2020

Related U.S. Application Data

(63) Continuation of application No. 15/474,788, filed on Mar. 30, 2017, now Pat. No. 11,173,283.

(60) Provisional application No. 62/315,076, filed on Mar. 30, 2016.

(51) Int. Cl.
| | |
|---|---|
| A61M 25/01 | (2006.01) |
| A61M 25/09 | (2006.01) |
| A61B 1/04 | (2006.01) |
| A61B 5/0215 | (2006.01) |
| A61B 5/026 | (2006.01) |

(Continued)

(52) U.S. Cl.
CPC .......... *A61M 25/0105* (2013.01); *A61B 1/04* (2013.01); *A61B 5/026* (2013.01); *A61B 5/0215* (2013.01); *A61B 5/6852* (2013.01); *A61M 25/0067* (2013.01); *A61M 25/013* (2013.01); *A61M 25/09041* (2013.01); *A61M 2025/0166* (2013.01); *A61M 2025/09116* (2013.01)

(58) Field of Classification Search
None
See application file for complete search history.

(56) References Cited

U.S. PATENT DOCUMENTS 4,858,810 A * 8/1989 Intlekofer .......... A61B 17/3403
                                                        24/115 M
5,137,288 A    8/1992 Starkey
(Continued)

OTHER PUBLICATIONS

International Search Report & Written Opinion, dated Dec. 3, 2015.

*Primary Examiner* — Benjamin S Melhus

(57) ABSTRACT

Torque devices for use with intravascular devices and associated systems and methods are disclosed. In some embodiments, a torque device for use with an intravascular device includes a first component having a body defining a tapered opening for receiving a proximal portion of the intravascular device, a first arm extending from the body, and a second arm extending from the body; and a second component movably coupled to the first component, wherein the second component is movable relative to the first component between an open position where the torque device is configured to slidably receive the proximal portion of the flexible elongate member between the first and second arms of the first component and a closed position where the torque device fixedly engages the proximal portion of the flexible elongate member between first and second arms of the first component.

17 Claims, 10 Drawing Sheets

(51) Int. Cl.
*A61B 5/00* (2006.01)
*A61M 25/00* (2006.01)

(56) References Cited

U.S. PATENT DOCUMENTS

| | | | | |
|---|---|---|---|---|
| 5,137,517 | A * | 8/1992 | Loney | A61M 25/09041 606/1 |
| 5,159,861 | A * | 11/1992 | Anderson | A61B 17/22 606/1 |
| 5,161,534 | A | 11/1992 | Berthiaume | |
| 5,392,778 | A * | 2/1995 | Horzewski | A61M 25/09041 600/434 |
| 5,851,189 | A | 12/1998 | Forber | |
| 6,030,349 | A * | 2/2000 | Wilson | A61M 25/09041 600/585 |
| 6,033,414 | A * | 3/2000 | Tockman | A61N 1/057 606/129 |
| 6,491,681 | B1 * | 12/2002 | Kunis | A61M 25/0136 604/528 |
| 6,872,192 | B2 * | 3/2005 | Nash | A61M 29/02 604/164.02 |
| 8,025,629 | B2 * | 9/2011 | Shelton | A61M 25/09041 81/487 |
| 8,038,628 | B2 | 10/2011 | von Malmborg et al. | |
| 9,770,574 | B2 * | 9/2017 | McArthur | A61M 25/01 |
| 10,675,010 | B2 * | 6/2020 | Schwarz | A61B 90/30 |
| 2003/0040735 | A1 * | 2/2003 | Kunis | A61M 25/0138 604/528 |
| 2004/0236214 | A1 | 11/2004 | Opie et al. | |
| 2005/0070820 | A1 * | 3/2005 | Boutillette | A61M 25/09041 604/528 |
| 2005/0240120 | A1 * | 10/2005 | Modesitt | A61M 25/09041 604/528 |
| 2007/0004991 | A1 * | 1/2007 | Shelton | A61M 25/09041 604/528 |
| 2007/0016105 | A1 * | 1/2007 | Mamourian | A61M 25/09041 600/585 |
| 2008/0262432 | A1 | 10/2008 | Miller | |
| 2008/0294030 | A1 | 11/2008 | von Malmborg et al. | |
| 2010/0100103 | A1 * | 4/2010 | Haskal | A61M 25/09041 606/108 |
| 2011/0306900 | A1 | 12/2011 | Whittaker et al. | |
| 2013/0066328 | A1 | 3/2013 | Singh | |
| 2013/0103001 | A1 | 4/2013 | BenMaamer et al. | |
| 2013/0150793 | A1 * | 6/2013 | Beissel | A61M 25/0105 604/171 |
| 2013/0190731 | A1 | 7/2013 | Cude | |
| 2013/0303330 | A1 | 11/2013 | Stevens et al. | |
| 2014/0187874 | A1 | 7/2014 | Burkett et al. | |
| 2014/0187920 | A1 | 7/2014 | Millett | |
| 2014/0203555 | A1 * | 7/2014 | Frankland | A61M 25/09 285/390 |
| 2014/0276225 | A1 * | 9/2014 | Moger | A61M 25/09 600/585 |
| 2015/0105650 | A1 * | 4/2015 | Burkett | A61B 1/3137 74/543 |
| 2015/0217090 | A1 | 8/2015 | Burkett | |
| 2015/0273187 | A1 | 10/2015 | Richardson | |
| 2016/0058977 | A1 | 3/2016 | Burkett et al. | |
| 2016/0067456 | A1 | 3/2016 | Burkett | |
| 2016/0073957 | A1 | 3/2016 | Szunyog | |

* cited by examiner

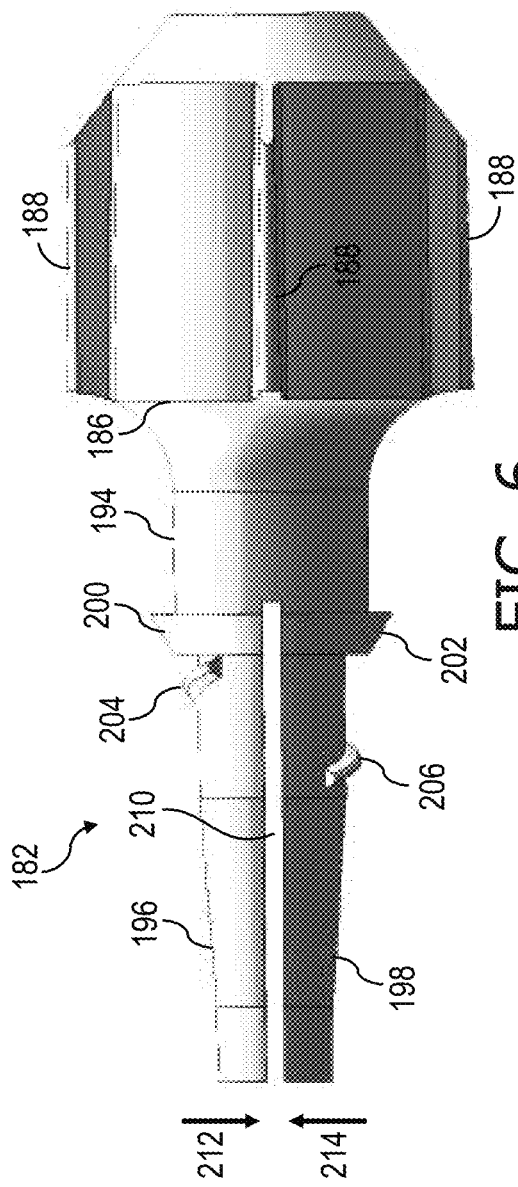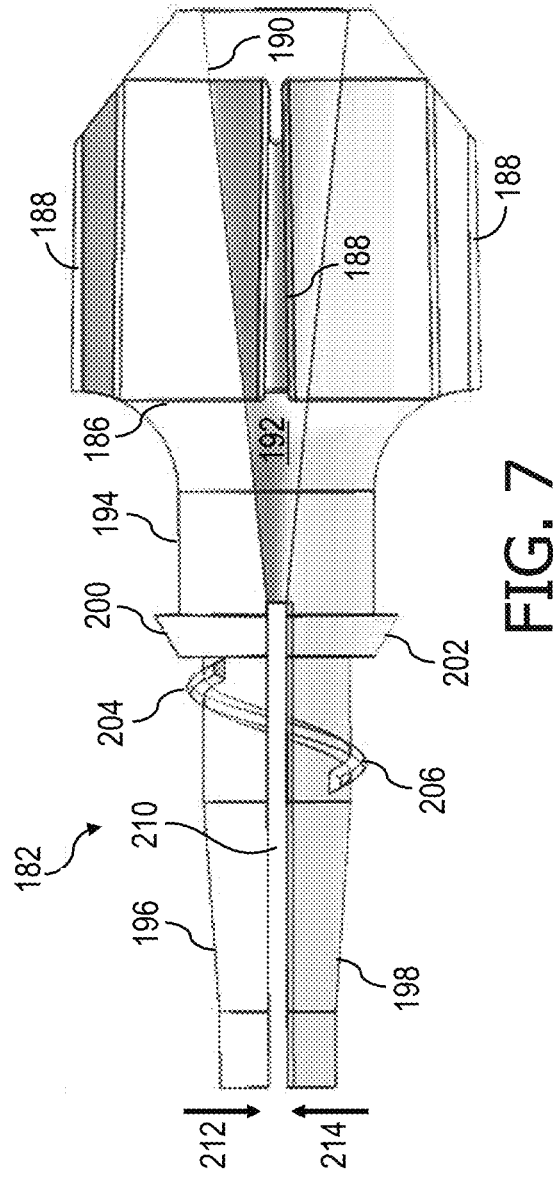

TORQUE DEVICES FOR USE WITH INTRAVASCULAR DEVICES AND ASSOCIATED SYSTEMS AND METHODS

CROSS-REFERENCE TO PRIOR APPLICATIONS

This application is a Continuation of Ser. No. 15/474,788, filed Mar. 30, 2017, which claims the benefit of U.S. Provisional Patent Application Ser. No. 62/315,076, filed Mar. 30, 2016. These applications are hereby incorporated by reference herein.

TECHNICAL FIELD

The present disclosure relates to torque devices for use with intravascular devices, systems, and methods.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel. To date, guidewires containing pressure sensors or other electronic components have suffered from reduced performance characteristics compared to standard guidewires that do not contain electronic components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guide wire.

Further, in many instances a torque device is positioned over a proximal portion of the intravascular device to facilitate steering of the intravascular device through vasculature. The torque device mechanically engages the outer surface of the intravascular device to provide an interface for the surgeon to manipulate the intravascular device. While existing torque devices have been adequate for previous intravascular device designs, they do not provide adequate mechanical and ergonomic functionality for some of the recent intravascular devices with improved handling characteristics. For example, some recent intravascular devices utilized embedded electrical leads within a polymer tubing to provide electrical connections. Some existing torque devices can damage (e.g., break, kink, short, etc.) these types of electrical connections during tightening and/or torqueing of the torque device. Further, some existing torque devices do not provide adequate holding strength and do not meet the ergonomic requirements of surgeons. Further still, some existing torque devices have complicated insertion/removal techniques that make it difficult to insert and/or remove the intravascular device without potentially damaging the intravascular device.

Accordingly, there remains a need for improved torque devices for use with intravascular devices.

SUMMARY

Embodiments of the present disclosure are directed to torque devices for use with intravascular devices, systems, and methods.

In some embodiments, a torque device for use with an intravascular device is provided. The torque device can include a first component having a body defining a tapered opening for receiving a proximal portion of the intravascular device, a first arm extending from the body, and a second arm extending from the body; and a second component movably coupled to the first component, wherein the second component is movable relative to the first component between an open position where the torque device is configured to slidably receive the proximal portion of the flexible elongate member between the first and second arms of the first component and a closed position where the torque device fixedly engages the proximal portion of the flexible elongate member between first and second arms of the first component.

In some embodiments, an intravascular system is provided that includes an intravascular device comprising: a flexible elongate member having a proximal portion and a distal portion; at least one sensing element secured to the distal portion of the flexible elongate member; and at least one communication line extending from the at least one sensing element to the proximal portion of the flexible elongate member; and a torque device configured to selectively interface with the proximal portion of the flexible elongate member, the torque device including: a first component having a body defining a tapered opening for receiving a proximal end of the flexible elongate member, a first arm extending from the body, and a second arm extending from the body; and a second component movably coupled to the first component, wherein the second component is movable relative to the first component between an open position where the torque device is configured to slidably receive the proximal portion of the flexible elongate member between the first and second arms of the first component and a closed position where the torque device fixedly engages the proximal portion of the flexible elongate member between first and second arms of the first component.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 6 is a side view of the component of FIGS. 4 and 5.

FIG. 7 is a side, partial phantom view of the component of FIGS. 4-6.

DETAILED DESCRIPTION

Figure 1:
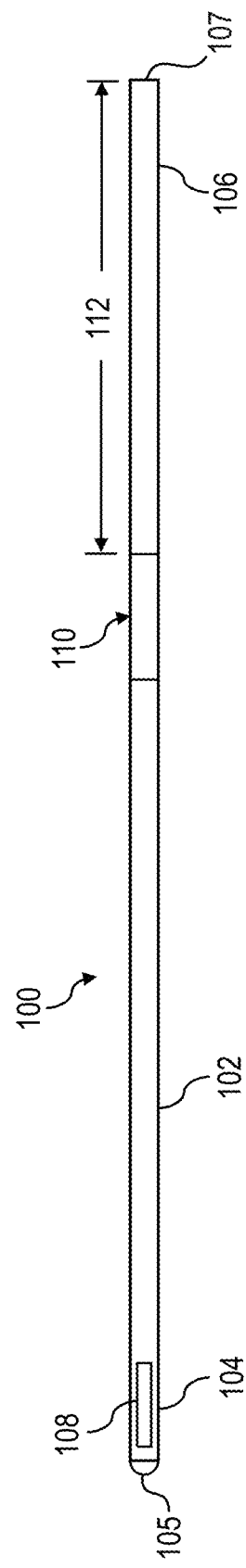
FIG. 1 is a diagrammatic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, intravascular catheters and intravascular guidewires. In that regard, intravascular catheters may or may not include a lumen extending along its length for receiving and/or guiding other instruments. If the intravascular catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an fro electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized. Further, in some instances the flexible elongate member includes multiple electronic, optical, and/or electro-optical components (e.g., pressure sensors, temperature sensors, imaging elements, optical fibers, ultrasound transducers, reflectors, mirrors, prisms, ablation elements, fro electrodes, conductors, etc.).

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal end 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Further, in some embodiments the connector 110 provides both electrical and optical connections to both electrical conductor(s) and optical communication pathway(s) coupled to the component 108. In that regard, it should again be noted that component 108 is comprised of a plurality of elements in some instances. In some instances, the connector 110 is configured to provide a physical connection to another device, either directly or indirectly. In other instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. Generally, any number of electrical conductors, optical pathways, and/or combinations thereof can extend along the length of the flexible elongate member 102 between the connector 110 and the component 108. In some instances, between one and ten electrical conductors and/or optical pathways extend along the length of the flexible elongate member 102 between the connector 110 and the component 108. For the sake of clarity and simplicity, the embodiments of the present disclosure described below include three electrical conductors. However, it is understood that the total number of communication pathways and/or the number of electrical conductors and/or optical pathways is different in other embodiments. More specifically, the number of communication pathways and the number of electrical conductors and optical pathways extending along the length of the flexible elongate member 102 is determined by the desired functionality of the component 108 and the corresponding elements that define component 108 to provide such functionality.

In some instances, the intravascular device 100 may include one or more features as described in one or more of U.S. Patent Application Publication No. 2014/0187874, filed Dec. 30, 2013 and titled "INTRAVASCULAR DEVICES, SYSTEMS, AND METHODS", U.S. Patent Application Publication No. 2015/0217090, filed Feb. 2, 2015 and titled "INTRAVASCULAR DEVICES, SYSTEMS, AND METHODS HAVING A CORE WIRE WITH EMBEDDED CONDUCTORS", U.S. Patent Application Publication No. 2015/0273187, filed Mar. 19, 2015 and titled "INTRAVASCULAR DEVICES, SYSTEMS, AND METHODS HAVING A CORE WIRE FORMED OF MULTIPLE MATERIALS," U.S. Patent Application Publication No. 2016/0058977, filed Aug. 27, 2015 and titled "INTRAVASCULAR DEVICES, SYSTEMS, AND METHODS HAVING AN ADHESIVE FILLED DISTAL TIP ELEMENT,"

U.S. Patent Application Publication No. 2016/0067456, filed Sep. 3, 2015 and titled "PRESSURE GUIDE WIRE PULL-BACK CATHETER," U.S. Patent Application Publication No. 2016/0073957, filed Sep. 10, 2015 and titled "INTRA-VASCULAR DEVICES, SYSTEMS, AND METHODS HAVING A SENSING ELEMENT EMBEDDED IN ADHESIVE," each of which is hereby incorporated by reference in its entirety.

Figure 2:
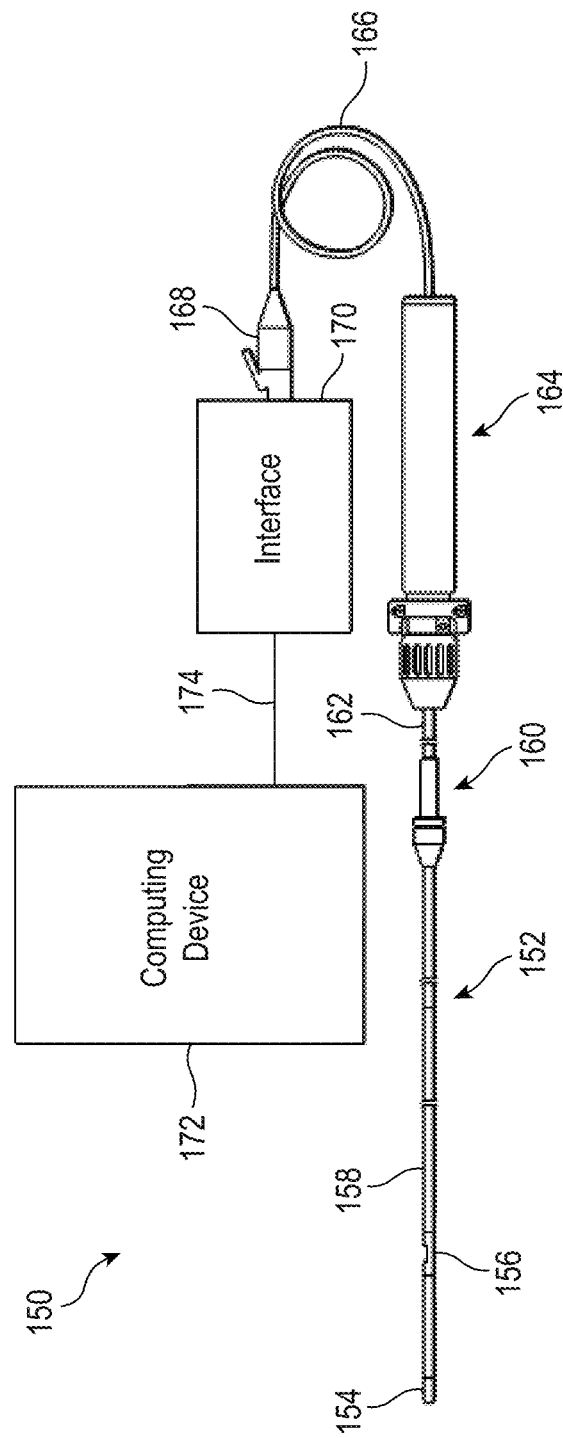
FIG. 2 is a diagrammatic schematic view of an intravascular system according to an embodiment of the present disclosure.

Referring now to FIG. 2, shown therein is a system 150 according to an embodiment of the present disclosure. As shown, the system 150 includes an instrument 152. In that regard, in some instances instrument 152 is an intravascular device as described above in the context of FIG. 1. Accordingly, in some instances the instrument 152 includes features similar to those discussed above with. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. Connector 164 will be described in greater detail below with reference to at least FIGS. 3-10. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure and, in particular, the processing and analysis techniques for the intravascular devices described in the context of FIG. 1. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., hand-held, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170. In such instances, the connector 168 (or other similar connector in communication with instrument 152) may plug into a port associated with computing device 172. Alternatively, the instrument 152 may communicate wirelessly with the computing device 172. Generally speaking, the communication pathway between the instrument 152 and the computing device 172 may have no intermediate nodes (i.e., a direct connection), one intermediate node between the instrument and the computing device, or a plurality of intermediate nodes between the instrument and the computing device.

Figure 3:
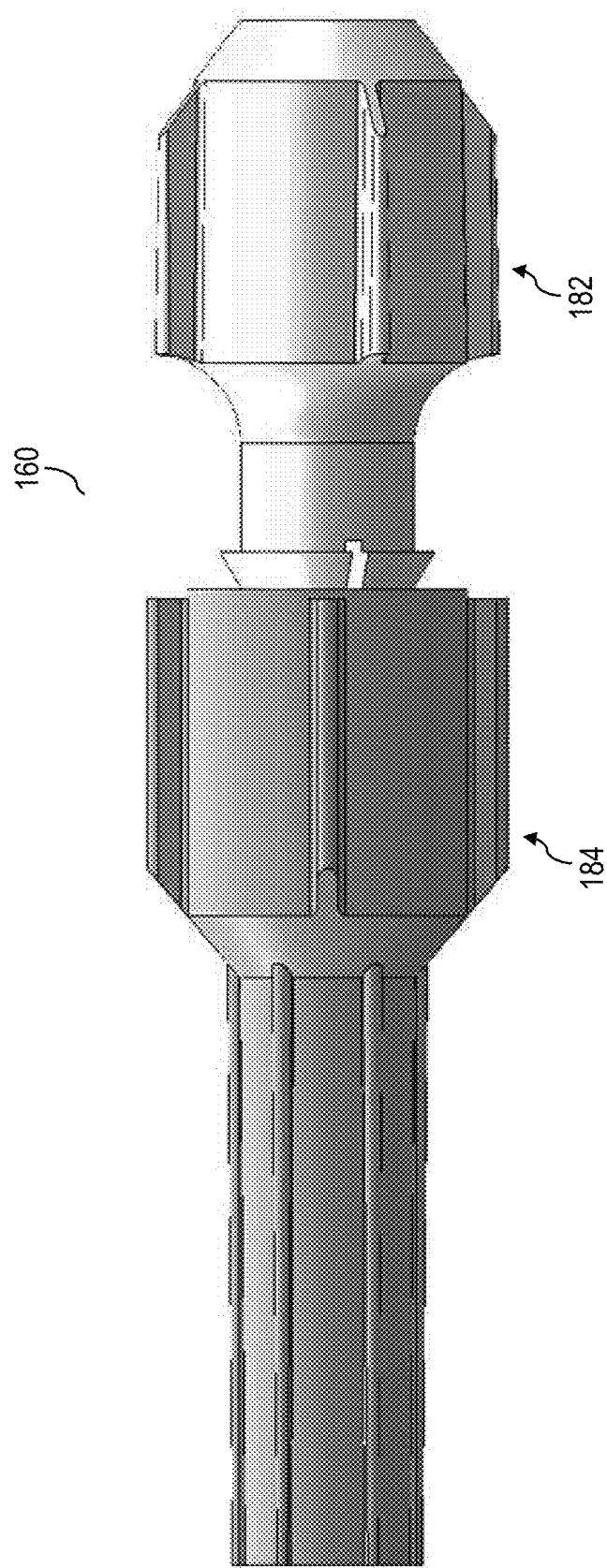
FIG. 3 is a side view of components of a torque device according to an embodiment of the present disclosure.

Referring now to FIG. 3, shown therein is a side view of the torque device 160 according to an embodiment of the present disclosure. The torque device 160 can include a component 182 and a component 184. The components 182 and 184 of the torque device 160 can engage each other via a snap feature. The snap feature can allow the components 182 and 184 to remain connected together while allowing the torque device 160 to move freely along the intravascular device 100, which can include frontline guide wires, sensing guide wires, peripheral guide wires, and/or other types of intravascular devices described above. Mating threaded features on the components 182 and 184 can allow a user to manually tighten the torque device onto the intravascular device 100. In this regard, projections, ridges, or other features on the outside surface(s) of the component(s) 182 and/or 184 can aid in rotating the components 182 and 184 with respect to one another, allowing the torque device 160 to tighten onto the intravascular device 100. Further, in some instances the components 182 and 184 have different grip diameters. In this regard, dual or multiple grip diameters can allow for selective coarse and fine rotation of intravascular device 100 based on the grip diameter of the torque device 160 being used by the user. The component 182 can include a tapered bore/opening that allows for easy insertion of the intravascular device 100. In this regard, a larger opening at an end of the component 182 can facilitate easier insertion of an end of the intravascular device 100 into the torque device 160. Further, in some instances the bore can be at least partially defined by multi-taper conforming extensions to provide an increased surface area for engaging with the intravascular device 100, which can allow for greater holding grip and prevent damage to embedded electrical leads or other components of the intravascular device. In this regard, the elongated contact area of the torque device 160, which can be in the range of ⅛" to ½" in length (e.g., an average engagement length of 3/16" in some implementations) or longer, can provide significant improvement in grip strength compared to the point contact designs employed on current torque device designs. Additional details of the torque device 160, including features of the components 182 and 184, will be discussed below.

Figure 4:
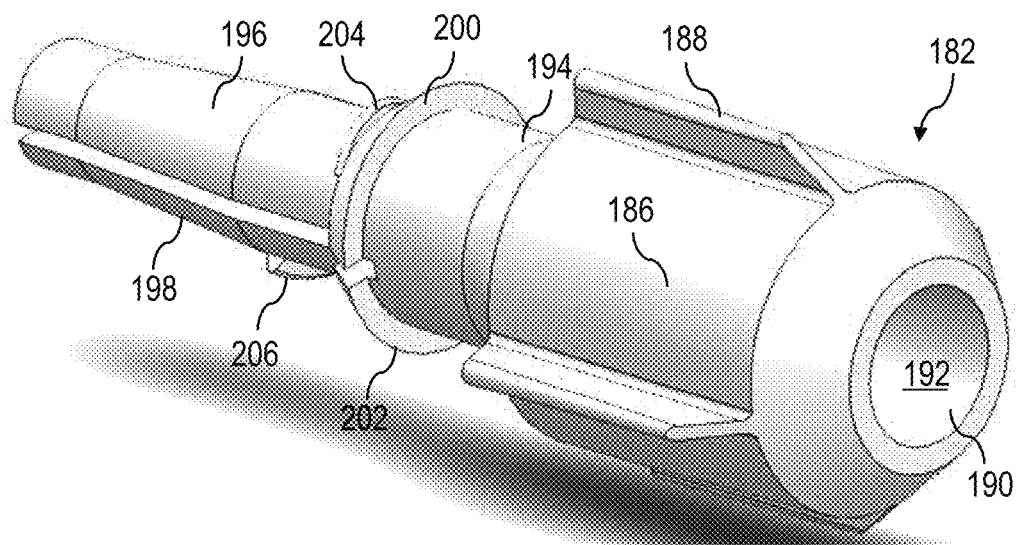
FIG. 4 is a perspective proximal view of a component of the torque device of FIG. 3 according to an embodiment of the present disclosure.
Figure 5:
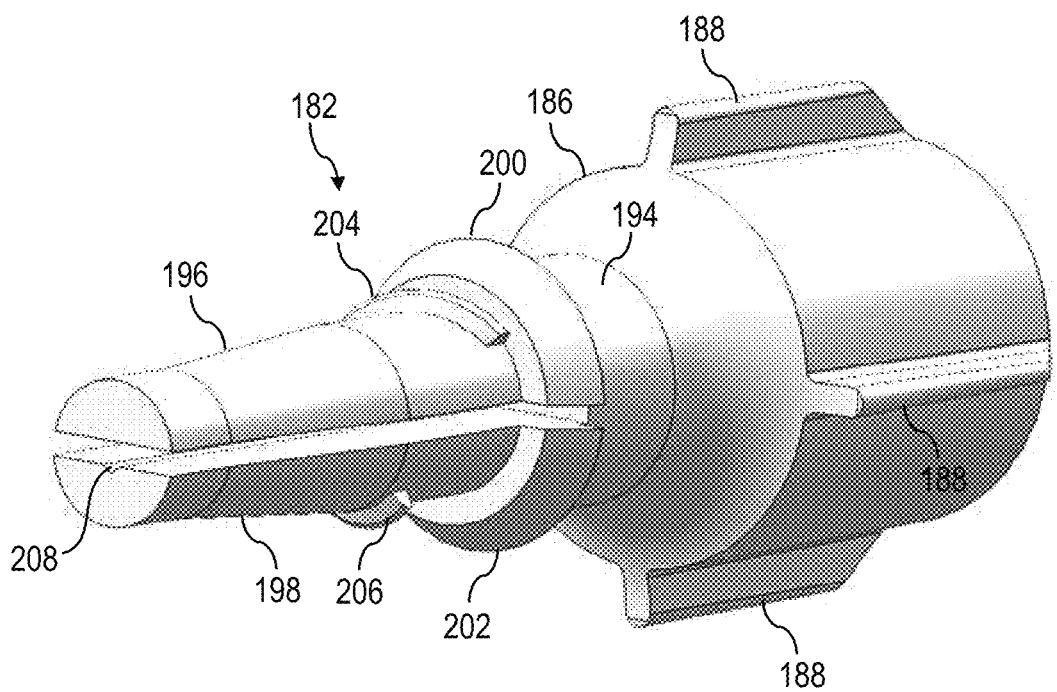
FIG. 5 is a perspective distal view of the component of FIG. 4.
Figure 8:
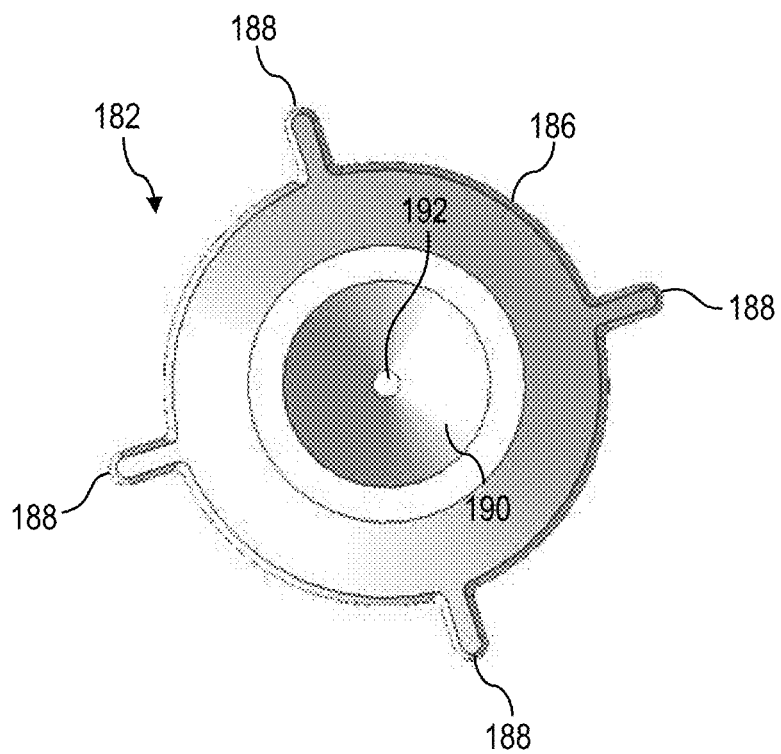
FIG. 8 is a proximal end view of the component of FIGS. 4-7.
Figure 9:
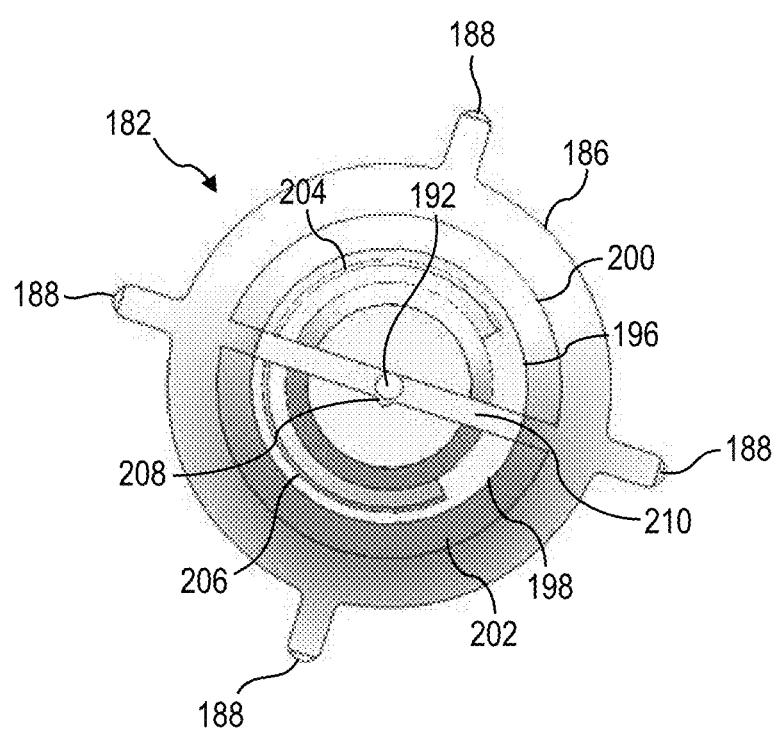
FIG. 9 is a distal end view of the component of FIGS. 4-8.

Referring to FIGS. 4-9, shown therein are details of the component 182. In this regard, FIG. 4 is a perspective proximal view of the component 182; FIG. 5 is a perspective distal view of the component 182; FIG. 6 is a side view of the component 182; FIG. 7 is a side, partial phantom view of the component 182; FIG. 8 is a proximal end view of the component 182; and FIG. 9 is a distal end view of the component 182. As shown, the component 182 includes a body 186. Gripping features 188 extend from the body 186. The gripping features 188 can include projections, ridges, textures (e.g., knurled surfaces), other features, and/or combinations thereof. In this regard, the gripping features 188 can aid a user in rotating the component 182 to either tighten the torque device 160 onto the intravascular device 100 and/or manipulate the intravascular device 100 with the torque device 160 when the torque device 160 is engaged with the intravascular device 100. In some instances the gripping features 188 of the component 182 have a different diameter (e.g., larger or smaller) than gripping features of the component 184. In this regard, dual or multiple grip diameters can allow for selective coarse or fine rotation of intravascular device 100 based on the grip diameter of the torque device 160 being used by the user.

The component 182 can include a tapered surface 190 that defines a tapered lumen 192. In some implementations, the component 182 can be configured to be positioned distal of the component 184 along the intravascular device 100 when in use. Accordingly, in such implementations the tapered surface 190 may extend toward a distal end of the component 182 such that the tapered lumen 192 can receive the proximal end of the intravascular device 100 when coupling the torque device 160 to the intravascular device 100. The tapered surface 190 may have a conical shape (as in the illustrated embodiment of FIGS. 4-9) or other suitable tapered shapes. In this regard, the tapered surface 190 allows the torque device 160 to have a relatively large opening for receiving the intravascular device 100, which can make inserting the intravascular device 100 into the torque device much easier. For example, adjacent the distal end of the component 182 the diameter of the lumen 192 can be three, four, five, six, or more times larger than the outer diameter of the intravascular device. The tapered surface 190 can guide the intravascular device 100 to a centered position with respect to the central longitudinal axis of the torque device 160 for subsequent engagement.

The body 186 of the component 182 includes a section 194 that leads to extensions 196 and 198. The extension 196 includes a tapered flange 200, while the extension 198 includes a tapered flange 202. The tapered flanges 200 and 202 can be utilized to facilitate snap-fit engagement of the component 182 with the component 184. In this regard, engagement of the component 182 with the component 184 via the tapered flanges 200 and 202 can cause the components 182 and 184 to remain coupled together in a loose, but connected fashion. For example, the components 182 and 184 can still be translated and/or rotated with respect to one another within a limited range, but the tapered flanges 200 and 202 can prevent or at least resist complete separation of the components 182 and 184 from one another.

The extensions 196 and 198 are configured to selectively engage with the intravascular device 100. In this regard, the extensions 196 and 198 are separated from one another in an open or neutral position (as shown by gap 210) and can be displaced towards one another (as indicated by arrows 212 and 214) for engagement with the intravascular device 100. For example, in some instances selective engagement of a tapered structure of the component 184 with the extensions 196 and 198 is utilized to selectively engage/disengage the torque device 160 with the intravascular device 100. In this regard, the tapered structure of the component 184 can cause the extensions 196 and 198 to move towards one another (as indicated by arrows 212 and 214) thereby pinching and/or clamping onto an intravascular device 100 positioned between the extensions 196 and 198.

In the illustrated embodiment the extension 196 includes a thread feature 204 and the extension 198 includes a thread feature 206. As best shown in FIG. 7, the thread features 204 and 206 can be arranged to define a single continuous thread feature for engagement with a corresponding thread feature of the component 184. In this regard, the amount of threaded engagement between component 182 and the component 184 can be used to selectively control the amount of displacement of the extensions 196 and 198 and, thereby, the amount of grip the torque device 160 exerts on the intravascular device 100. For example, rotation of the components 182 and 184 relative to one another about the thread features 204 and 206 can cause translation of the components 182 and 184 with respect to one another to vary which part of a tapered structure (e.g., a conical bore, tapered planar surface(s), etc.) of the component 184 engages the extensions 196 and 198.

One or both of the extensions 196 and 198 can include a surface feature to facilitate engagement and/or alignment of the intravascular device 100 with the torque device. For example, as best shown in FIG. 9, a recess 208 can be formed in the extension 198. The recess 208 can be sized and shaped to receive the intravascular device 100 such that when the intravascular device 100 is gripped between the extensions 196 and 198 the intravascular device 100 is maintained within the recess 208. This can prevent expulsion of the intravascular device from between the extensions 196 and 198 and/or prevent unwanted kinking of the intravascular device 100 within the torque device 160.

Figure 10:
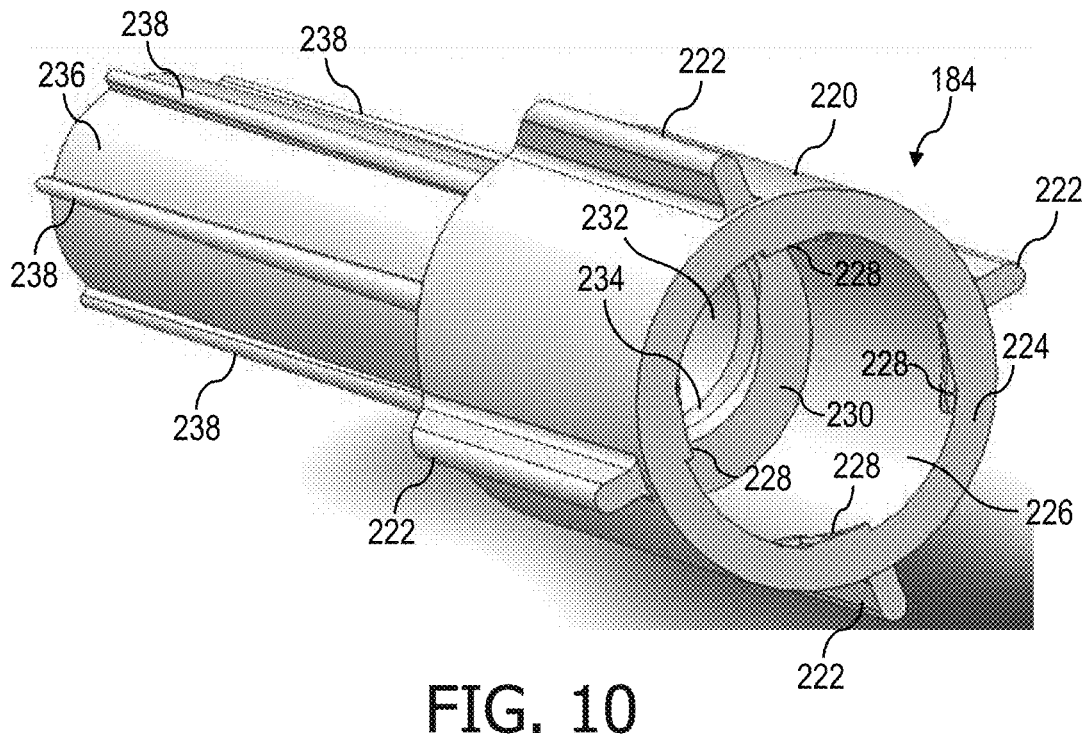
FIG. 10 is a perspective proximal view of another component of the torque device of FIG. 3 according to an embodiment of the present disclosure.
Figure 11:
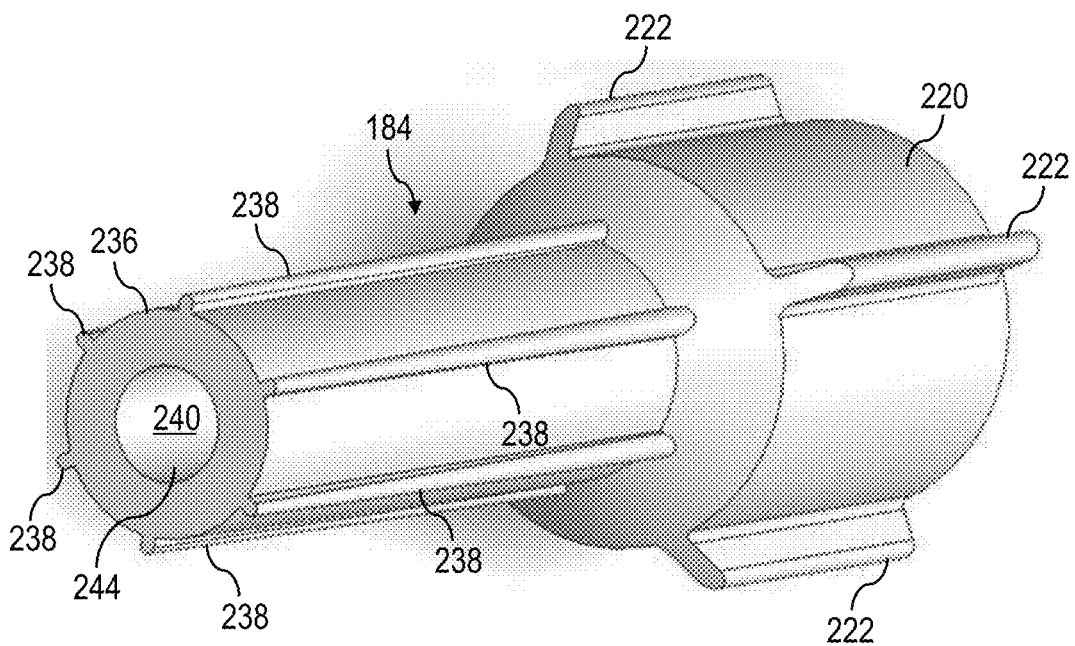
FIG. 11 is a perspective distal view of the component of FIG. 10.
Figure 12:
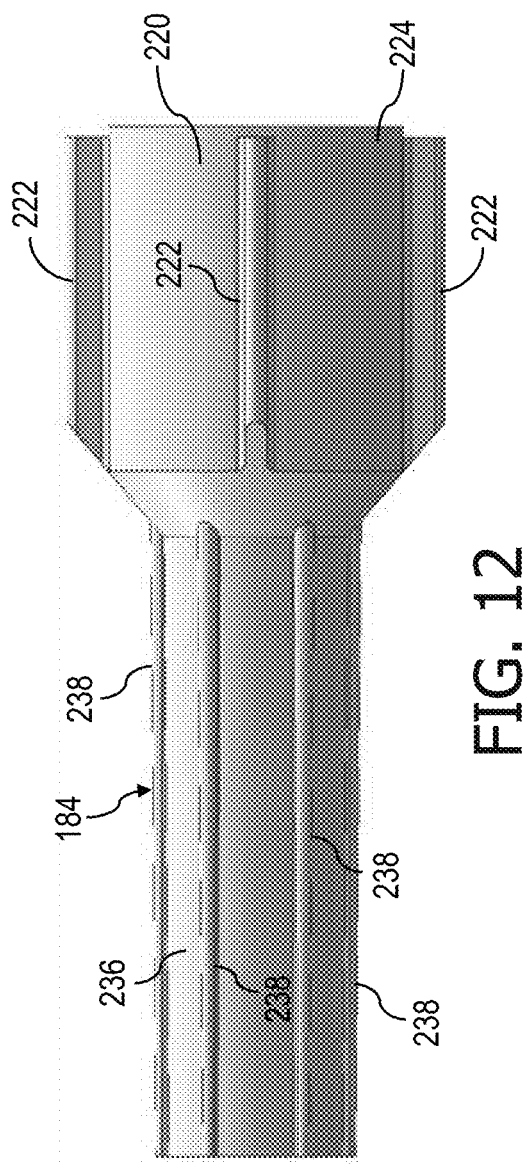
FIG. 12 is a side view of the component of FIGS. 10 and 11.
Figure 13:
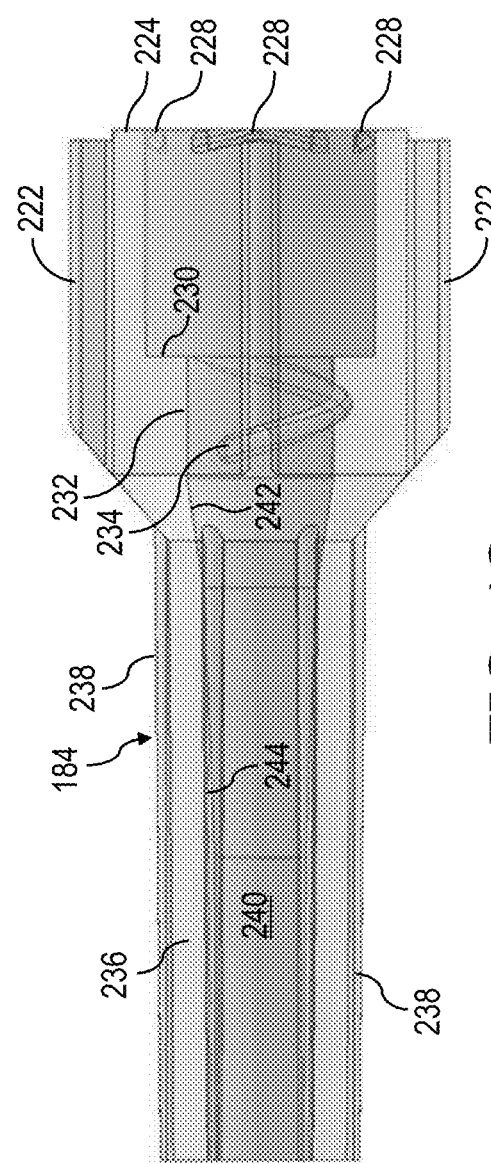
FIG. 13 is a side, partial phantom view of the component of FIGS. 10-12.
Figure 14:
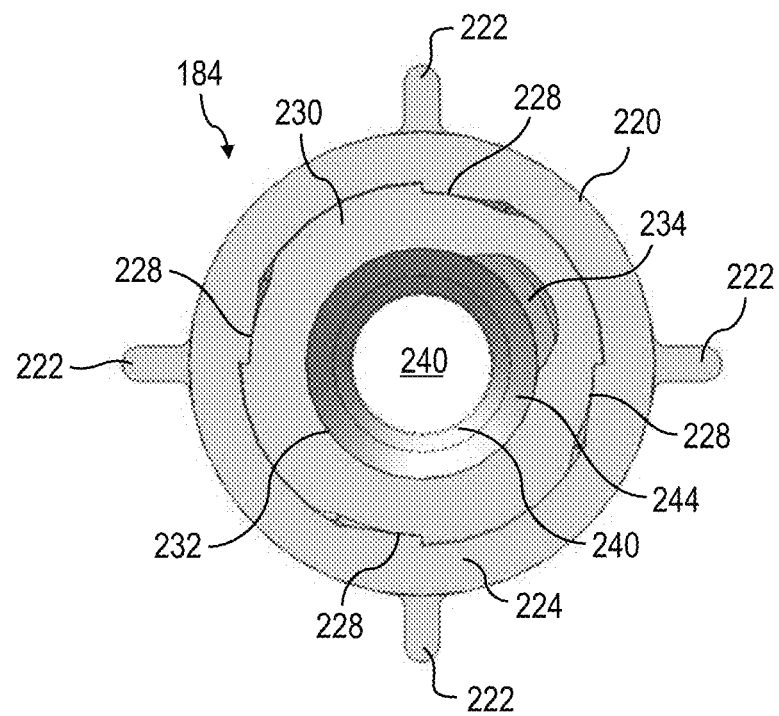
FIG. 14 is a proximal end view of the component of FIGS. 10-13.
Figure 15:
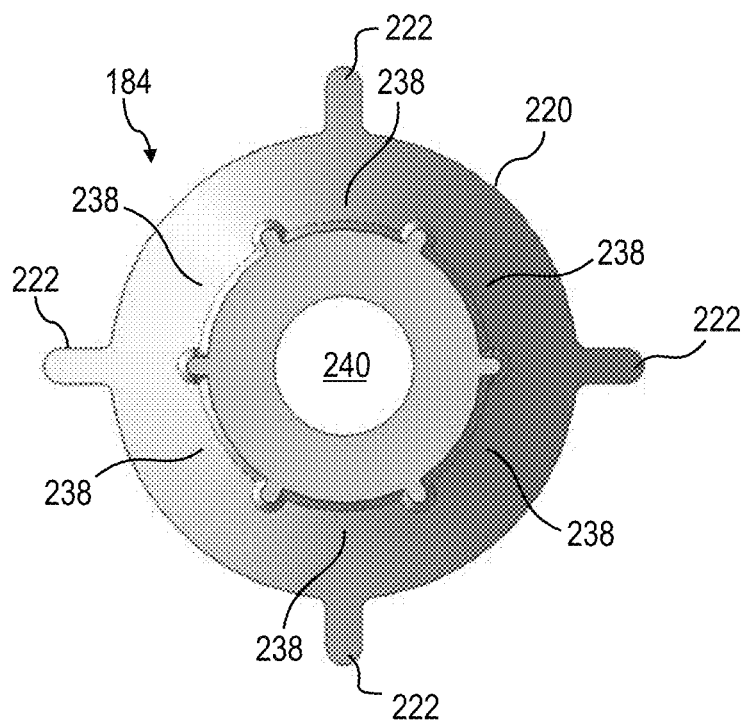
FIG. 15 is a distal end view of the component of FIGS. 10-14.

Referring to FIGS. 10-15, shown therein are details of the component 184. In this regard, FIG. 10 is a perspective proximal view of the component 184; FIG. 11 is a perspective distal view of the component 184; FIG. 12 is a side view of the component 184; FIG. 13 is a side, partial phantom view of the component 184; FIG. 14 is a proximal end view of the component 184; and FIG. 15 is a distal end view of the component 184. As shown, the component 184 includes a body 220. Gripping features 222 extend from the body 220. The gripping features 222 can include projections, ridges, textures (e.g., knurled surfaces), other features, and/or combinations thereof. The component 184 can include an extension 236 extending proximally from the body 220. Gripping features 238 can extend from the extension 236. The gripping features 238 can also include projections, ridges, textures (e.g., knurled surfaces), other features, and/or combinations thereof. In this regard, the gripping features 188, 222, and 238 of the components 182 and 184 can aid a user in rotating the components 182 and 184 to either tighten the torque device 160 onto the intravascular device 100 and/or manipulate the intravascular device 100 with the torque device 160 when the torque device 160 is engaged with the intravascular device 100. In some instances one or more of the gripping features 188, 222, and 238 have a different diameter (e.g., larger or smaller) than another of the gripping features 188, 222, and 238. In this regard, dual or multiple grip diameters can allow for selective coarse or fine rotation of intravascular device 100 based on the grip diameter of the torque device 160 being used by the user.

The component 184 can include a distal end 224 that defines an opening 226. In some implementations, the component 184 can be configured to be positioned proximal of the component 182 along the intravascular device 100 when in use. Accordingly, in such implementations the distal end 224 can be configured to receive and interface with a proximal end of the component 182. For example, in the illustrated embodiment the component 184 includes projections 228 around the opening 226. The projections 228 are configured to interface with the tapered flanges 200 and 202 of the component 182. For example, as the component 182 is introduced into the opening 226 of the component 184, the projections 228 can slide over the tapered surfaces of the flanges 200 and 202. Once past the tapered flanges 200 and 202, the engagement of the projections 228 with the flat distal side of the tapered flanges 200 and 202 can prevent or at least resist complete separation of the components 182 and 184.

The component 184 can include an internal shoulder 230. A surface 232 can extend proximally from the shoulder 230. The shoulder 230 and surface 232 can include a thread feature 234. As best shown in FIG. 13, the thread feature 234 can be a female thread feature configured to interface with the thread features 204 and 206 of the component 182. In other implementations, the thread feature 234 can be a male thread feature and the component 182 can include one or more female thread features. The amount of threaded engagement between component 182 and the component 184 can be used to selectively control the amount of displacement of the extensions 196 and 198 and, thereby, the amount of grip the torque device 160 exerts on the intravascular device 100. For example, rotation of the components 182 and 184 relative to one another about the thread features 204 and 206 can cause translation of the components 182 and 184 with respect to one another to vary which part of a tapered lumen 240 engages the extensions 196 and 198. In this regard, as best seen in FIG. 13, the tapered lumen 240 can be defined by surfaces 232, 242, and 244. In this regard, tapered surface 242 extends proximally from surface 232. Tapered surface 244 extends proximally from surface 244 to a proximal end of the component 184. In this regard, the tapered surface 244 can be configured to interface with the extensions 196 and 198 of the component 182 to cause selectively displacement of the extensions 196 and 198 towards one another. The tapered surfaces 242 and 244 may have a conical shape (as in the illustrated embodiment) or other suitable tapered shapes (e.g., opposed planar surface(s)). As the extensions 196 and 198 are advanced further proximally into the lumen 240, the amount of displacement of the extensions 196 and 198 towards one another will be increased due to the narrower dimensions of the tapered lumen 240. Accordingly, by controlling the displacement of the components 182 and 184 relative to one another the amount of grip on the intravascular device 100 can be correspondingly controlled.

Figure 16:
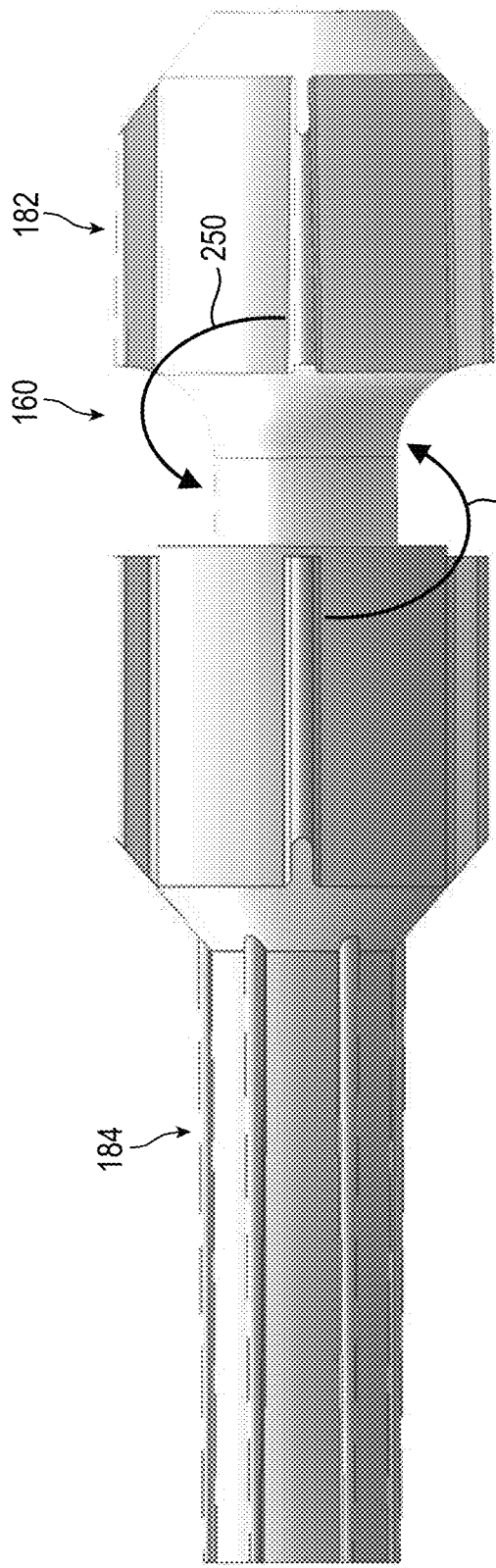
FIG. 16 is a side view of the torque device of FIG. 3 in an open position according to an embodiment of the present disclosure.
Figure 17:
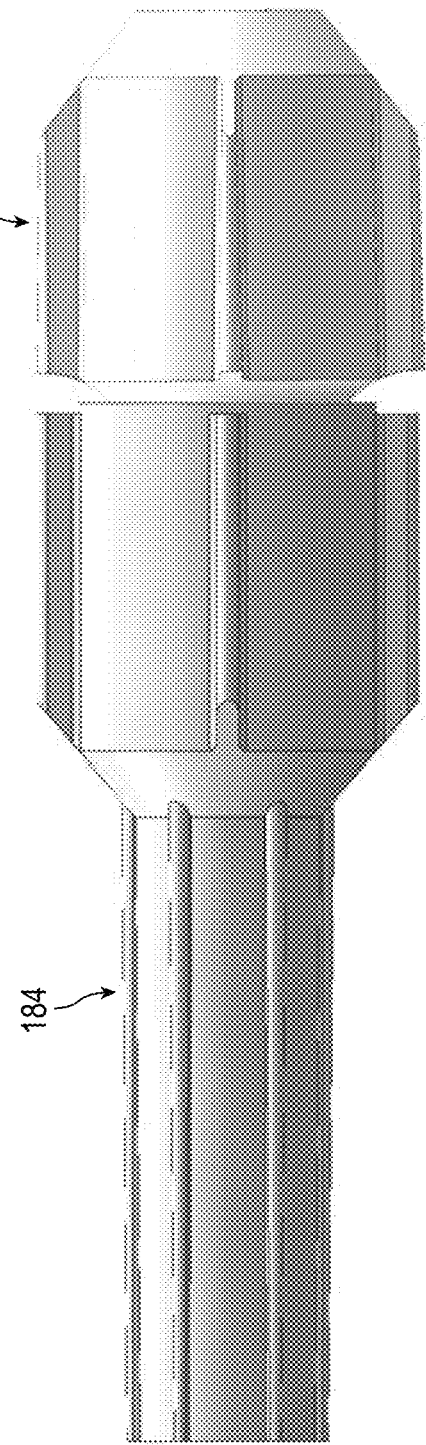
FIG. 17 is a side view of the torque device of FIGS. 3 and 16 in a closed position according to an embodiment of the present disclosure.

Referring now to FIGS. 16 and 17, the torque device 160 can be moved between an open position in which it can receive and slide along the intravascular device 100 and a closed positioned in which it can fixedly engage with an outer surface of the intravascular device 100. In this regard, FIG. 16 is a side view of the torque device 160 in an open position; and FIG. 17 is a side view of the torque device 160 in a closed position. As shown in FIG. 16, rotation of the component 182 along path 250 relative to the component 184 and/or rotation of the component 184 along path 252 relative to the component 182 can cause the torque device to move from the open position to the closed position. As discussed above, by controlling the amount of rotation of the components 182 and 184 relative to one another, relative displacement of the extensions 196 and 198 of the component 182 can be controlled and, thereby, the amount of grip on the intravascular device 100 can be correspondingly controlled.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A torque device for use with an intravascular device, the torque device comprising:
   a first component comprising:
      a body defining an opening for receiving a proximal portion of the intravascular device;
      a first arm extending from the body;
      a second arm extending from the body;
      a space disposed between the first arm and the second arm; and
      only a single thread wrapped around the first arm and the second arm such that:
         the single thread does not complete a full revolution;
         a first length of the single thread is disposed on a first side of the first component;
         a second length of the single thread is disposed on an opposite, second side of the first component and the second length is greater than the first length; and
      a second component movably coupled to the first component,
   wherein the proximal portion of the intravascular device is configured to extend within the space between the first arm and the second arm, wherein the first arm and the second arm are movable relative to one another to grip the proximal portion of the intravascular device.

2. The torque device of claim 1, wherein the first arm includes a recess sized and shaped to receive and engage the proximal portion of the intravascular device.

3. The torque device of claim 2, wherein the second arm includes a planar surface to engage the proximal portion of the intravascular device.

4. The torque device of claim 1, wherein the body further includes a central lumen in communication with the opening, the central lumen sized and shaped to slidably receive the proximal portion of the intravascular device.

5. The torque device of claim 4, wherein the second component is further configured to couple to the first component via a snap-fit engagement.

6. The torque device of claim 5, wherein the first component includes a tapered flange and the second component includes at least one projection for the snap-fit engagement with the tapered flange of the first component.

7. The torque device of claim 6, wherein the at least one projection extends inwardly towards a central lumen of the second component.

8. The torque device of claim 1, wherein the first component and the second component are in threaded engagement via the single thread.

9. The torque device of claim 8,
wherein the single thread comprises a male thread disposed on an outer surface of the first component, and
wherein an inner surface of the second component includes a female thread.

10. The torque device of claim 8, wherein the second component is movable relative to the first component between: an open position where the torque device is configured to slidably receive the proximal portion of the intravascular device between the first arm and the second arm of the first component; and a closed position where the torque device fixedly engages the proximal portion of the intravascular device between the first arm and the second arm of the first component.

11. The torque device of claim 10, wherein rotation of the second component relative to the first component through the threaded engagement moves the second component between the open position and the closed position.

12. The torque device of claim 1,
wherein the proximal portion of the intravascular device is fixedly engaged over only a single contact area,
wherein the single contact area is disposed between the first arm and the second arm of the first component,
wherein the single contact area has a length of at least 0.33 inches.

13. The torque device of claim 1,
wherein a first portion of the second component comprises a first plurality of radial projections extending longitudinally along the second component and separated from one another along the second body component by a first spacing,
wherein a second portion of the second component comprises a second plurality of radial projections extending longitudinally along the second component and separated from one another along the second component by a second spacing different than the first spacing.

14. The torque device of claim 13,
the first portion of the second component is configured to permit a first amount of rotation of the intravascular device when the first portion of the second component is gripped by a user; and
the second portion of the second component is configured to permit a second amount of rotation of the intravascular device when the second portion of the second component is gripped by the user, wherein the second amount of rotation is different than the first amount of rotation.

15. The torque device of claim 1, wherein the torque device includes only the first component and the second component.

16. The torque device of claim 1, wherein the opening of the first component is tapered.

17. The torque device of claim 1,
wherein the single thread comprises a first thread portion disposed on the first arm and a second thread portion disposed on the second arm,
wherein the first thread portion and the second thread portion are separated from one another by the space, and
wherein the first thread portion and the second thread portion are offset longitudinally relative to one another.

* * * * *